United States Patent [19]

Linkow

[11] Patent Number: 5,102,336
[45] Date of Patent: Apr. 7, 1992

[54] NECKLESS BLADE IMPLANT

[76] Inventor: Leonard I. Linkow, 1530 Palisades Ave., Fort Lee, N.J. 07024

[21] Appl. No.: 303,944

[22] Filed: Jan. 30, 1989

Related U.S. Application Data

[63] Continuation-in-part of Ser. No. 252,290, Sep. 30, 1988.

[51] Int. Cl.⁵ .............................................. A61C 8/00
[52] U.S. Cl. .................................................... 433/176
[58] Field of Search .............................. 433/173, 176

[56] References Cited

U.S. PATENT DOCUMENTS

| | | | |
|---|---|---|---|
| 3,683,501 | 8/1972 | Edelman | 433/176 |
| 3,837,080 | 9/1974 | Paqualini | 433/176 |
| 3,992,780 | 11/1976 | Herskovits | 433/176 |
| 4,002,284 | 1/1977 | Suppus | 228/115 |
| 4,024,638 | 5/1977 | Linkow et al. | 433/176 |
| 4,081,908 | 4/1978 | Sneer | 433/176 |
| 4,223,412 | 9/1980 | Aoyagi et al. | 433/176 X |
| 4,521,192 | 6/1985 | Linkow | 433/176 X |
| 4,531,917 | 7/1985 | Linkow et al. | 433/176 |
| 4,600,388 | 7/1986 | Linkow | 433/176 |
| 4,661,066 | 4/1987 | Linkow et al. | 433/176 |
| 4,762,492 | 8/1988 | Nagai | 433/176 X |
| 4,799,886 | 1/1989 | Wimmer | 433/176 |
| 4,804,132 | 2/1989 | DiFrancesco | 228/115 |
| 4,997,383 | 3/1991 | Weiss et al. | 433/176 |

FOREIGN PATENT DOCUMENTS

| | | | |
|---|---|---|---|
| 2454414 | 5/1975 | Fed. Rep. of Germany | 433/176 |
| 2717615 | 10/1978 | Fed. Rep. of Germany | 433/176 |
| 2193640 | 2/1988 | United Kingdom | 433/176 |

*Primary Examiner*—Robert P. Swiatek
*Assistant Examiner*—Nicholas D. Lucchesi
*Attorney, Agent, or Firm*—Darby & Darby

[57] ABSTRACT

An oral implant for supporting an artificial tooth structure has an implant portion adapted to be fitted in an opening in a bone of a patient in the vicinity of the occlusal plane. At least one post portion having first and second ends is provided for attachment to the implant portion. The first end of the post is adapted to receive at least a part of the artifical tooth structure. The second end is adapted for a direct connection to a connection part of the implant portion. The post portion has lateral dimensions which are at least substantially as wide as the upper surface of the implant portion.

43 Claims, 4 Drawing Sheets

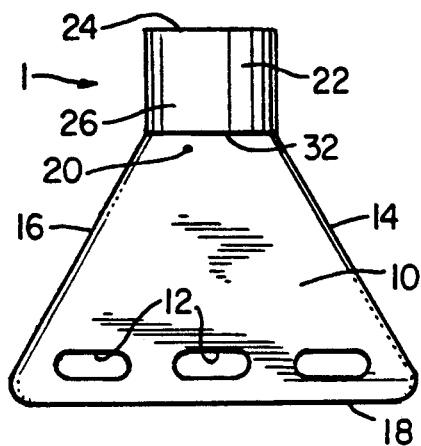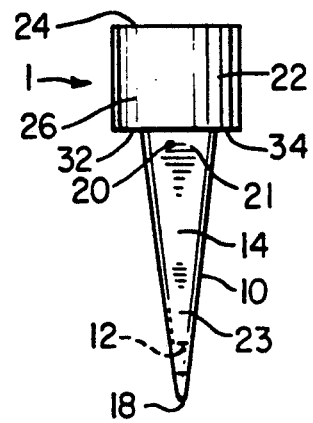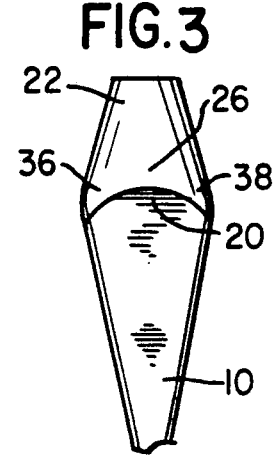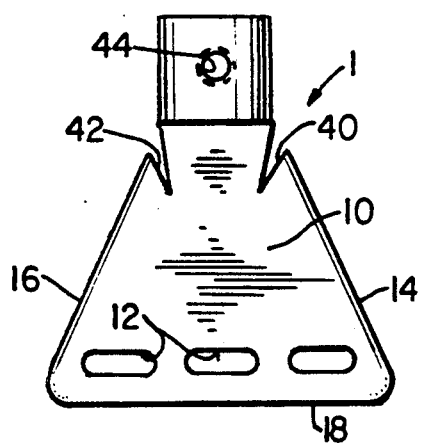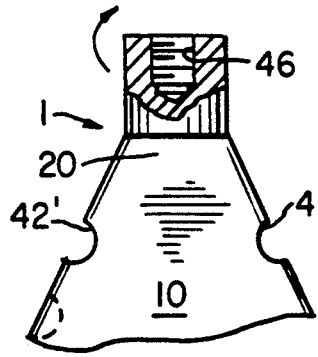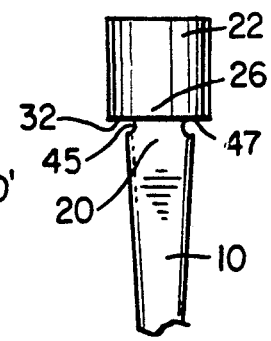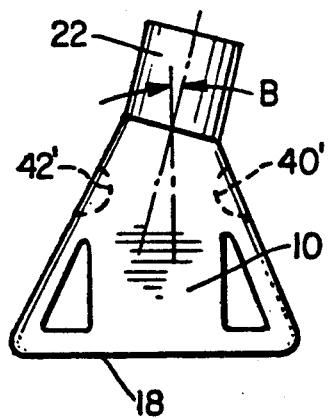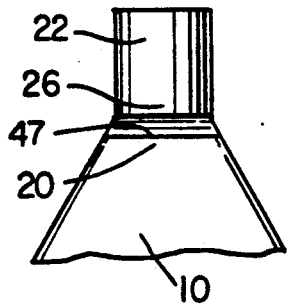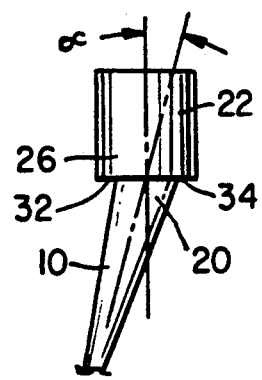

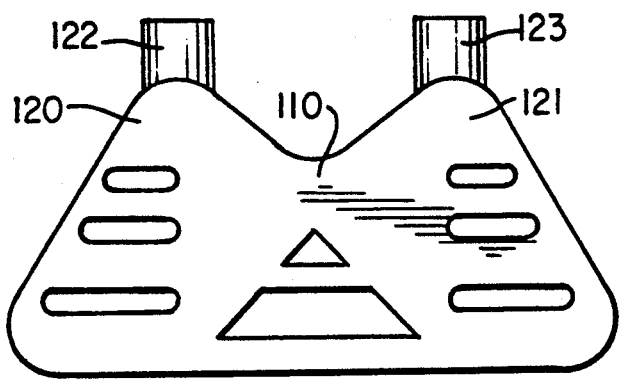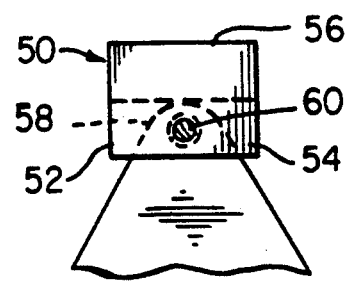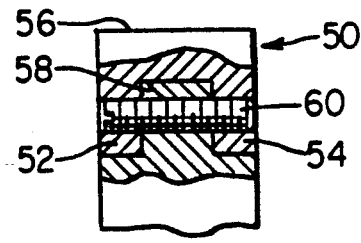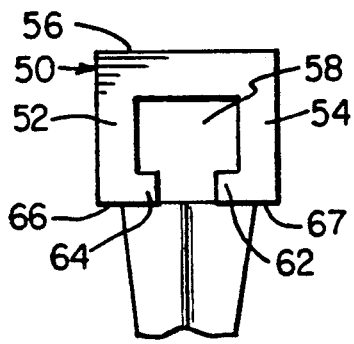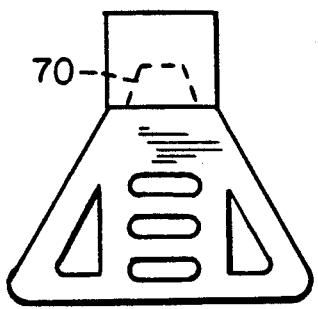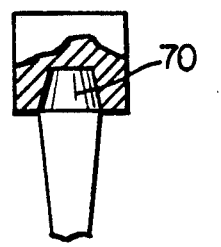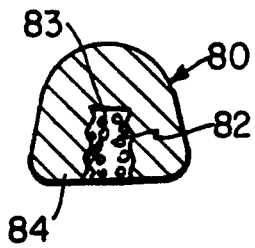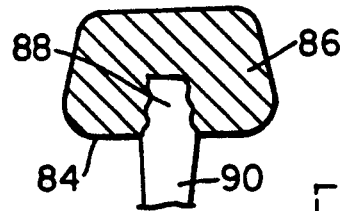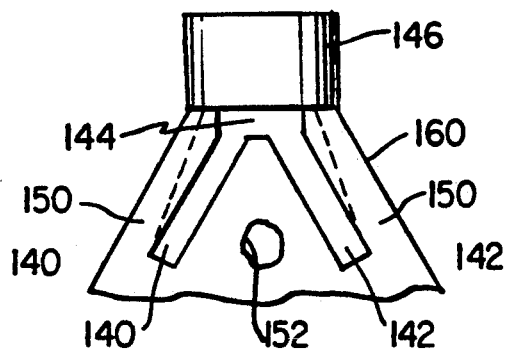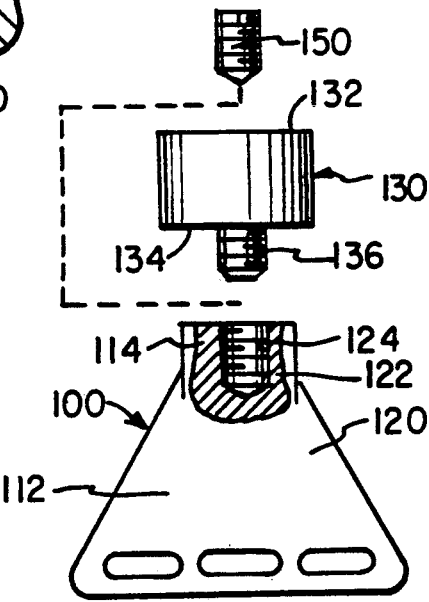

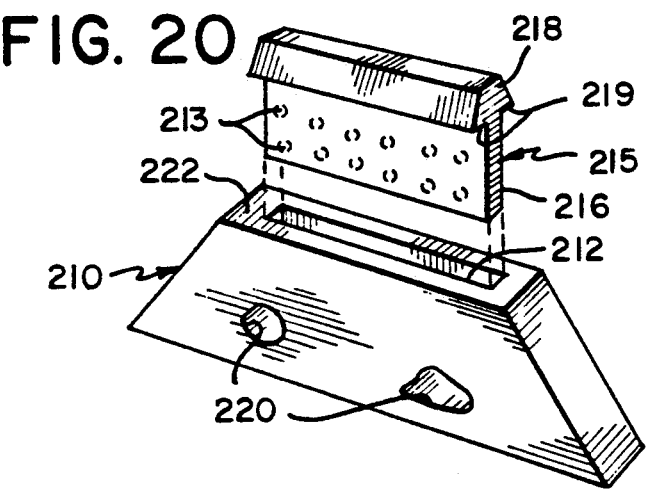
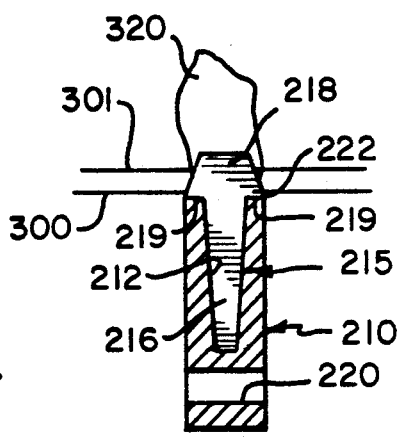
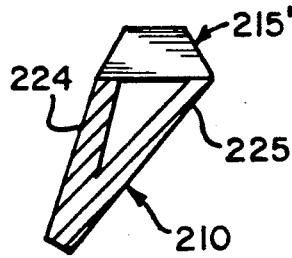
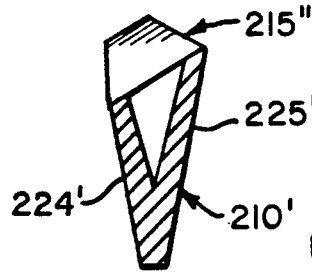
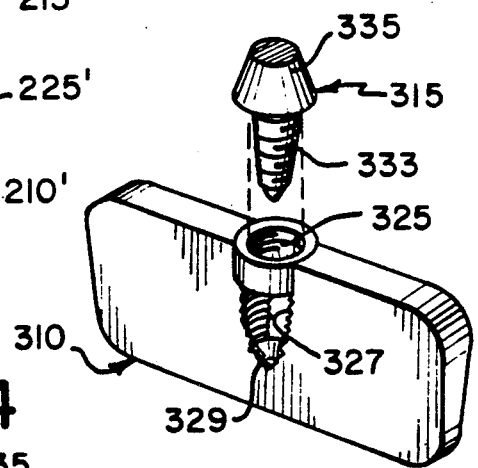
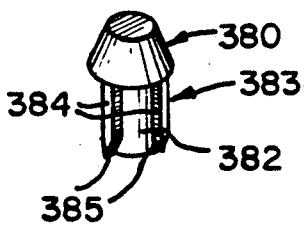
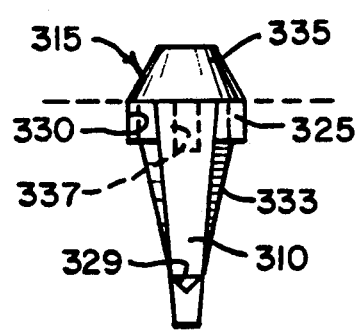
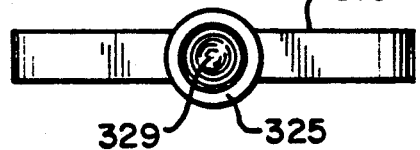

NECKLESS BLADE IMPLANT

This application is a continuation-in-part of U.S. patent application Ser. No. 252,290 filed Sept. 30, 1988.

BACKGROUND OF THE INVENTION

This invention relates to dental implants and, more particularly to blade type implants having posts without necks.

A dental implant, such as that described in U.S. Pat. Nos. 3,465,441 and 3,660,899 of the present inventor, is used to support an artificial bridge, tooth or other dental prosthesis. The implant has an implant portion, e.g. in the form of a blade, that is secured in the underlying bone in an edentulous span. A post portion, typically with a narrowed neck part, extends up from the implant portion and supports the artificial bridge or crown. This type implant is inserted by making an incision in the fibromucosal tissue down to the underlying alveolar ridge crest bone. The tissue is then reflected to expose the bone and a burr is used to create a groove in the bone which is as deep as the implant portion The implant portion is then wedged into the bone. After the insertion, the tissue is sutured about the neck part so that the rest of the post protrudes above the tissue line. Typically, a few weeks or months are allowed to pass before the dental prosthesis is attached to the post. During this period, bone starts to grow around the implant portion and through holes provided in it, thereby acting to anchor the implant in place before it is stressed by use.

Submergible blade implants, such as that shown in U.S. Pat. No. 4,177,562 of A. L. Miller and A. J. Viscido, allow a blade to be inserted in the jawbone for a long period of time before being placed in actual use. With this type of implant the blade is completely submerged in the bone. It is then covered over with tissue and allowed to remain in place for several months. For this period it is protected against being dislodged by the tongue or other teeth during mastication. Once there has been substantial regrowth of the bone over, around and through the submerged blade, the tissue is again opened and the post is attached to the blade, typically by a screw connection. In order to accommodate the screw, however, it is necessary for the implant body or blade to be relatively wide, at least in the area of the screw. This limits the use of the implant in patients with narrow ridge crest bones. In addition a collar is frequently provided at the location of the screw, which collar projects out of the bone and the gum tissue as in the design disclosed in the Miller patent mentioned above. As a result of this collar bacteria can invade the tissue around the implant, which may lead to an infection that causes the implant to fail.

When a semi-submerged implant is used, i.e. an implant wherein a screw collar projects out of the bone, the collar is sometimes used as an abutment to support overlying provisional dentures. Such use can easily loosen the implants during the healing stages, since only one or two of these collars act as the sole support of the denture. Also, even if the provisional dentures are hollowed out so as to be larger in diameter than the collars and to thereby avoid contact with them, food and other debris can become lodged in this space created under the dentures. The decay of this food can cause tissue breakdown with subsequent implant failure.

As noted, it is common for many types of prior oral implants to have a post with a neck portion which connects to a blade. Such a neck portion is typically much narrower than the rest of the post and the blade. In view of that, a step-type transitioned area is defined between the post and the blade. The steep variations between the dimensions of the blade, post and the neck make the transitioned area subject to a much greater concentration of the stresses of mastication than other areas of the implant. All this makes the design of the narrow neck the weak spot of the oral implants disclosed by the prior art. In use, such implants can bend in the area of the neck portion when chewing movements are performed. This can cause bone resorption immediately below the neck portion and breakage of the neck.

U.S. Pat. No. 4,178,686 to Riess et al. provides an oral implant in which the implant portion is a polymer matrix having spherical particles of tricalciumphosphate ceramic embedded in its exterior. A post portion has an elongated core member extending substantially into the implant portion. The base of the top part of the post portion extends to the outer edges of the implant portion and tapers inward in the part towards the artificial tooth support. The tooth support itself may be attached to the post by means of a threaded shaft. With this arrangement, the forces of mastication are resisted solely by the threaded shaft, which is relatively narrow, and/or the narrow core portion of the post.

The present inventor's own U.S. Pat. No. 4,600,388 discloses a blade in which the post is designed to straddle recessed portions in the blade. Because of these recessed portions in the blade, the post does not extend beyond the outer limits of the blade. Further, the legs of the implant, that allow it to straddle the blade, are relatively thin and these thin legs must resist the forces of mastication. With this implant there is no direct means for rigidly securing the post to the blade, other than the natural spring force of the legs of the post.

Sometimes the major portion of bone is such that an implant located in the middle of the bone would position an artificial tooth at an angle which would cause it to be out of alignment with other teeth To solve this problem, various devices are proposed in the present applicant's U.S. Pat. No. 4,713,004.

The relatively narrow neck portions of posts in prior art implants are subject to bending and breakage during normal use. When this occurs it is often necessary to remove part or all of the implant, including the blade portion, to repair the damage. Thus, it would be extremely advantageous if blade implants could be provided with extremely rugged post portions which could easily resist the forces of mastication.

SUMMARY OF THE INVENTION

The present invention provides an oral blade-type implant for supporting an artificial tooth structure in which the traditional narrowed neck portion of the support post is eliminated.

In an illustrative embodiment of the invention, the oral implant for supporting an artificial tooth structure includes an implant portion in the form of a blade. This blade is adapted to be fitted in an opening in the patient's mandible or maxilla in the vicinity of the occlusal plane. On the edge of the blade directed toward the occlusal plane, the blade has at least one connection part that projects toward the occlusal plane. The installation of the blade in the bone is such that at least a portion of the connection part extends out of the bone. At least one post portion is adapted to receive at least a part of the artificial tooth structure at the end and is directly connected to the connection part of the implant portion at its base or other end. The post has a size at its base such that it extends outwardly from sides of the connection part, defining shoulders for supporting the post on the blade.

In a preferred embodiment the blade or implant portion has a substantially triangular configuration. The connection portion of the implant part is positioned at the apex of the triangle and the shoulders of the base of the post extend laterally from the plane of the triangle. In particular, the shoulders of the base of the post overlap surfaces on the connection part of the implant portion in the bucco-lingual direction. Also the shoulders may extend from the connection part of the implant portion in the bucco-lingual direction. A cross-section of the implant portion in the bucco-lingual direction may have a wedge-shaped configuration.

The implant portion may be provided with a bending arrangement to enable the oral implant to be bent in the mesio-distal direction. The bending arrangement is achieved with a pair of V-shaped slits, one on each side of the connection part.

In a still further embodiment the post portion is detachably connected to the implant portion and the second or base end of the post portion is adapted to straddle the connection part of the implant portion. The base of the post portion has a pair of spaced apart legs and the connection part of the implant portion has a pair of recesses. In the assembled condition of the oral implant the legs fit within the recesses of the implant portion.

An implant with a detachable post may be designed so that the blade portion, including the connection part, is totally submerged in the bone during installation. A healing cap is located over the connection part to prevent bone growth over it. Subsequently the cap is removed and the post is installed.

Another embodiment utilizes a screw which is partly secured in the implant blade and partially threads into the surrounding bone to provide a combination blade-screw implant.

BRIEF DESCRIPTION OF THE DRAWINGS

The foregoing and other features of the present invention are described with reference to exemplary embodiments, which are intended to explain and not to limit the invention, and are illustrated in the drawings in which:

FIG. 1 is a front view of a dental implant according to the present invention;

FIG. 2 is a side view of the dental implant of FIG. 1;

FIG. 3 is a side view of another embodiment of the dental implant;

FIG. 4 is a front view of still another embodiment of the dental implant illustrating bending notches;

FIG. 5 is a partial view of a further embodiment of the dental implant showing bending recesses;

FIG. 6 is a front view of an additional embodiment of the invention showing the post at an angle in the mesial-distal direction;

FIG. 7 is a side view of a still further embodiment of the invention with notches for bucco lingual bending;

FIG. 8 is a front view of FIG. 7;

FIG. 9 is a side view of another embodiment of the invention showing the post at an angle in the bucco-lingual direction;

FIG. 10 is a front view of a dental implant with two posts;

FIG. 11 is a partial front view of a still further embodiment of the dental implant with a removable post having connecting legs;

FIG. 12 is a side view of FIG. 11 partially in cross section;

FIG. 13 is a partial side view of another embodiment of the dental implant;

FIG. 14 is a front view of a still further embodiment of the dental implant with a removable post having a cavity;

FIG. 15 is a side view of FIG. 14;

FIG. 16 is a cross-sectional side view of one embodiment of a removable post with a cavity;

FIG. 17 is a partially-sectioned side view showing a connection between the post of FIG. 16 and a blade;

FIG. 18 is a front view of a semi-submergible oral implant;

FIG. 19 is a cross-sectional side view of an implant designed with legs that extend into the cortical plates and straddle the inferior alveolar;

FIG. 20 is a perspective view of an implant with a removable post that fits in a slit in the top of the blade;

FIG. 21 is a side cross section of an implant like that in FIG. 20, but with a tapered connection part;

FIGS. 22A and 22B are cross sections of implants with removable posts which are offset at an angle to the blade similar to the implant of FIG. 9;

FIG. 23 is a perspective view of a submergible combined blade and screw type implant prior to installation of the screw in the blade;

FIG. 23A is a perspective view of another embodiment of a screw for the implant of FIG. 22;

FIG. 24 is a side view of the implant of FIG. 23 with the screw installed;

FIG. 25 is a top view of the implant of FIG. 23;

DESCRIPTION OF ILLUSTRATIVE EMBODIMENTS

Figure 26:
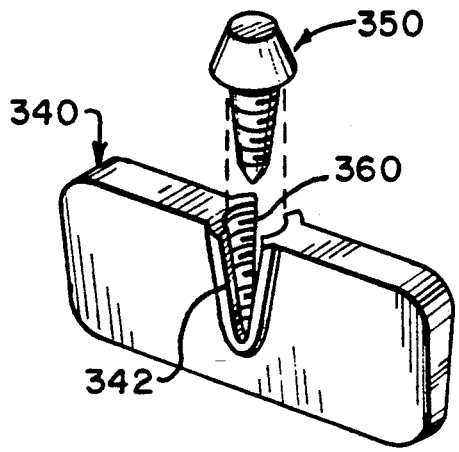
FIG. 26 is a perspective view of a further embodiment of a submergible combined blade and screw type implant with a blade body having a lateral bulge and a removable post.

Although specific embodiments of the invention will now be described with reference to the drawings, it should be understood that the embodiments shown are by way of example only and are merely illustrative of some of the many possible specific embodiments which can represent applications of the principles of the invention. Various changes and modifications that are obvious to one skilled in the art to which the invention pertains, are deemed to be within the spirit, scope and contemplation of the invention as further defined in the appended claims.

In FIG. 1 there is shown an enlarged view of an oral implant made according to the present invention. The oral implant 1 includes an implant portion in the form of a blade 10 and a post portion 22. In the embodiment of FIG. 1, the blade and the post are permanently attached to each other.

The blade 10 has holes or vents 12 which allow bone to grow completely through the blade so as to anchor the implant in place.

It is shown in FIG. 1 that the blade in the mesio-distal plane has a substantially triangular configuration with rounded off edges. However, other configurations of the blade are possible. The triangular blade 10 has sides 14 and 16 and a base 18. The width of the base 18 (shown in FIG. 2) should be such as to allow tight engagement with an opening in a bone of the patient in which the implant is inserted.

A connection part 20 is located at the apex of the triangular blade i.e. opposite the base 18. The post portion 22 has a first end 24 and a second or base end 26 which is attached to the connection part 20. The first end 24 receives at least a part of the artificial tooth structure. The base end 26 is adapted for a direct connection to the blade 10 without any intermediary elements This connection is such that parts 32 and 34 in the bucco-lingual direction of the base 26 (FIG. 2) extend outwardly from the connection part of the blade. These extensions define a pair of shoulders for receiving and supporting the artificial tooth structure. Also, by keeping the apex or connection portion of the blade to the post as wide as possible, there will not be any weakness in the area which would otherwise cause bending or loss of bone.

FIG. 2 shows that the blade 10 in the bucco-lingual plane has a wedge-shaped configuration with wide end 21 and a narrow end 23. The connection part 20 of the plate is positioned at the wide end 21 of the wedge-shaped plate. Further, it can be seen that the narrow neck common to prior art devices has been eliminated. Instead, the post is even thicker than the blade over its entire length in the bucco-lingual direction. This allows the post to resist the forces of mastication. In the view of FIG. 1 it can also be seen that the connection part 20 and the post 22 have great thickness in the mesial-distal direction so that a rigid structure in all directions is obtained.

In the embodiment of the invention illustrated in FIG. 3, wings 36 and 38 of the base 26 of the post, overlap a top portion of the connection part 20 in the bucco-lingual direction. This makes the transition between the post and the blade smoother, reducing even further the stresses common to the neck-type oral implants.

To facilitate bending of the oral implant in the mesio-distal direction to align the artificial tooth with remaining natural teeth, a bending arrangement is provided within the blade of the invention. This bending arrangement is illustrated in FIG. 4 and includes at least two V-shaped slits or cavities 40, 42 extending from the outer surfaces of the sides 14, 16 into the body of the blade. The cavities 40, 42 are positioned at an angle to and equidistantly spaced from the base 18 of the blade. However, alternative configurations of the cavities are possible. For example, FIG. 5 shows cavities 40′ and 42′ with a semi-circular design.

The cavities of FIGS. 4 and 5 can be located at different heights on the implant. For example cavity 42′ could be located at a lower point such as shown in dotted line on FIG. 5. When the post is bent in the mesial-distal direction, as shown by the arrow in FIG. 5, notch 42′ tends to move upwardly and notch 40′ tends to move downwardly so that the grooves tend to end up at about the same height as shown in dotted line in FIG. 6.

If, in order to align the post 22 with other teeth along the occlusal plane, an angle of inclination B (FIG. 6) of the post 22 to the blade 10 in the mesio-distal direction is needed, the implant may be bent as described. However, as an alternative, the oral implant may be manufactured by casting or otherwise with its post permanently positioned at the angle B with respect to the blade in the mesio-distal direction. This angle may be, for example, 15°. In such a case the cavities 40′, 42′ shown in FIG. 5 need not be provided.

FIGS. 7 and 8 show an oral implant having a bending arrangement which facilitates bending in the bucco-lingual direction. The bending arrangement of these figures includes two grooves 45 and 47 extending along both sides of the blade 10. The grooves are positioned at the connection part 20 of the blade. Thus the post may be bent in the direction of the arrows of FIG. 7.

The embodiment of FIG. 9 is manufactured with the post 22 positioned at an angle α to the blade 10 in the bucco-lingual direction. Similar to the embodiment of FIG. 6, the embodiment of FIG. 9 can be used when the required angle of inclination is known in advance. Also, implants of this type can be cast with several standard offset angles for selection by the oral surgeon, e.g. 15°, 25°, etc.

The oral implant can have one post portion, as is shown in FIG. 1, or a plurality of the posts attached to the same blade. FIG. 10, illustrates an embodiment having two post portions 122 and 123 attached to the same blade 110. There are two connection parts 120 and 121 in the blade 110, each adapted to receive the individual post portion. A plurality of the posts can be used when a better support of an artificial dental structure by the oral implant is needed, e.g., to support dental bridges etc.

The posts can be circular, oval or rectangular with tapered or non-tapered outside walls. They may also be any other convenient shape.

The crown or the bridge can be attached to the oral implant by a screw or screws which pass through an opening in the crown or bridge into either horizontal threaded holes 44 in the post as shown in FIG. 4 or vertical threaded holes 46 as shown in FIG. 5. The vertical threaded hole and the screw inserted therein can be extended to penetrate through the post into the blade.

The oral implant of the invention can be provided with a post or posts removable from the blade. In that case (see FIGS. 11-13) a post 50 is provided with legs 52 and 54 projecting outwardly from the first end 56 of the post. In an assembled condition of the oral implant, the legs 52 and 54 straddle a projection 58 of the blade connection part Initially it can be merely a frictional connection between the legs and the connection portion as shown in FIGS. 11 and 12. As shown in FIG. 13 the legs can have inward projections 62 and 64 that snap into grooves in the connection portion.

To provide a fixed connection between the post and the blade, a screw 60 (FIGS. 11 and 12) can be used. This screw passes through threaded openings in the legs 52 and 54 of the post and a threaded opening in the projecting part 58 of the connection portion.

FIG. 13 further shows that legs 52 and 54 are made wider than the connection part of the blade, thus providing bucco-lingual shoulders 66, 67 for support of the artificial tooth structure.

The embodiment of FIGS. 11-13 may be made similar to the embodiment of FIG. 3, in that the lower parts of the legs can be extended to overlap the top portion of the connection part in the bucco-lingual direction (not shown in the drawings).

The post shown in FIGS. 14 and 15 does not have legs for engagement with the connection part of the blade. Instead, a cavity 70 is arranged in the central area of the second end of the post. The cavity 70 extends from an outer surface of the base of the post and is adapted to closely receive the connection part of the blade. A vertical or horizontal screw can be used to fixedly attach the post to the blade.

The oral implant of the invention can be installed by first making an incision in the fibromucosal tissue down to the underlying bone. The tissue is then reflected and a groove is drilled in the bone using a burr. This groove is made about the width of the base of the blade. The blade can then be snugly fit therein in such a manner that at least a portion of the connection part of the blade extends beyond the plane of the bone. In some instances, the connection part can be positioned just below the rim of the opening in the bone, allowing the second end of the overlapping post (e.g. surfaces 32, 34 in FIG. 2) to rest on the bone. Once the blade is in place, the tissue is sutured over the blade and around the post. Several weeks or months are allowed to pass before the dental prosthesis is attached to the post. During this period, the bone starts to grow around the implant portion and through the holes 12 provided in it until the surrounding bone becomes integrated with the blade. This is necessary to anchor the implant in place before it is stressed by use.

If a unitary blade and post are used, the next step is to install the artificial tooth structure on the post. If a separable post is used, the post must be attached to the connection part, e.g. by screws, before the prosthesis is installed.

The use of screws and similar devices for the attachment of a post to a blade requires additional space for drilling of threaded holes in these elements of the implant. Placement of such a threaded connection can be time consuming and not always reliable. The present invention offers a new way of connecting the blade and the post which allows the oral surgeon to avoid the above disadvantages of the threaded connections.

In FIGS. 16 and 17, there is shown a post 80 with an inside cavity 82 that extends from an outer surface 84 of the base end 86 into its body. The cavity is designed for close engagement with the connection part 88 of a blade 90. At least the connection part 88 of the blade is made from a material softer than the material of the post.

A plurality of tiny rigid bubbles or rigid three dimensional raisings extend from the surface of the cavity 83. One or more rough areas are thus defined by the bubbles within the surface 83. These bubbles can be created during the process of casting the post or may be etched therein The post can be connected to the blade by positioning the cavity of the post over the end of the connection part 88. A mallet or similar tool may be used to force the cavity 83 of the post onto the connection part 88 of the blade. As a result, the rigid bubbles of the post are crushed as the cavity is penetrated deeply by the connection part of the blade. This results in a cold weld locking of the two pieces together.

The various parts of each of the embodiments may be made of titanium, vitalium or surgical stainless steel. In the case of the embodiment of FIGS. 16 and 17, the relative hardness of these materials should be considered in selecting the materials, and typically the post and blade would be made of different materials.

A semi-submergible dental implant 100 is shown in FIG. 18. This implant includes an implant portion 112 and a post portion 130 which are manufactured as two separate pieces. A connection part 120 of the implant portion is positioned at a place of connection between the implant portion and the post portion. The connection part 120 has a receiving element 114 for receiving at least a part of the post. The receiving element 114 extends outwardly from the implant portion in the direction of the occlusal plane for a short distance, e.g. 2-3 mm.

The post portion 130 has a first end 132 and a second or base end 134. The first end receives at least a part of the artificial tooth structure. The base end 134 is adapted for a direct engagement with the receiving element of the implant portion. The receiving element 114 has a lateral dimension as wide as the lateral dimension of the base end 134 of the post.

A fastening member 136 protrudes outwardly from the base end 134. The receiving element 114 has an opening 124 for receiving the fastening member 136. In the embodiment of FIG. 18 the fastening member 136 and the opening 124 have threads for mutual engagement.

The opening 124 is also adapted to receive a cap or plug 150. The plug is designed to be threaded into the opening for the closing thereof. The plug and the implant can be made from the same material, e.g. titanium, vitalium or surgical stainless steel, preferably covered with hydroxylapatite. As an alternative the plug can also be made of Teflon or another suitable plastic.

The implant of FIG. 18 is installed in a manner similar to that discussed above. However, a groove is drilled in the bone deep enough for the implant portion 112 to be submerged in the groove below its upper rim in such a manner that only the receiving element 114 of the connection part 120 protrudes outwardly from the groove in the direction of the occlusal plane. However, element 114 is so short it does not extend significantly above the gum tissue. Once the implant portion is in place, the plug 150 is threaded into the opening 124. The gum tissue is then sutured over the implant portion and about the receiving element. As a result, only a very small part of the implant portion protrudes above the tissue. Thus the implant is protected from impact with the patient's tongue and other teeth.

During the waiting period the surrounding bone and tissue became integrated with the implant portion. However, the plug 150 prevents tissue growth in the opening 124.

Once the dentist is sure that the implant portion is firmly anchored in the bone, a new incision is made in the tissue and the plug is removed. In place of the cap, the post 130 is threaded into the opening 124.

When a patient's alveolar ridge bone 160 is wide, a groove can be made across the ridge bucco-lingually or labio-platally so as to span the soft medullary bone and include the tougher cortical bone near the surface of the ridge. In such a case the blade can be made with a cross section like that in FIG. 19. The blade of FIG. 19 has buccal and lingual legs 140, 142 connected by a transverse connection part 144 upon which post 146 is located As shown, the outer edges of the legs are received in the cortical plate 150 but circumvent the inferior alveolar nerves 152 by straddling them. In this manner the implant can take advantage of the maximum available bone by extending into the area near or in the cortical bone, while avoiding the nerves.

The shape of the front of the implant of FIG. 19 may be like any of the other designs in this application or in common use. Also the cross-sectional shape may be modified in any convenient manner to conform to existing bone and nerve conditions. For example the legs may be parallel and vertical, instead of slanted toward each other as in FIG. 19. Also, the legs may slant away from each other and the portions surrounding the nerve may form a smooth curve. In determining which shapes to use or fashion, CAT scans and tomograms may be used to locate the nerve and to define the bone structures.

As with the other implants discussed, the implant of FIG. 19 may be made semi-submergible by making the post detachable from the blade.

The implant shown in FIG. 18 is termed a semi-submergible implant because the receiving part 114 extends above the bone line. The device illustrated in FIG. 20, however, is a completely submergible blade with a detachable post.

The implant shown in FIG. 20 has a blade 210 which may be triangular, trapezoidal or rectangular in shape. For purposes of illustration a trapezoidal blade is shown in FIG. 20. On the upper surface 222 the blade is provided with a longitudinal slit 212 which is adapted to receive a longitudinal extension 216 of a post 215. Attached to an upper portion of extension 216 is a portion 218 adapted to receive an artificial tooth structure. The shoulders 219 on part 218 extend over the width of the blade as better shown in FIG. 21. The projection part 216 may have parallel sides as shown in FIG. 20 or tapered sides as shown in FIG. 21.

As best shown in FIG. 21 the blade 210 is placed in a cavity formed in bone 300. During the insertion of the blade portion the post 215 is not connected to the blade. However, a cap may be fitted in the slot 212 to prevent growth of bone over the upper surface of the blade. Tissue 301 is then sutured over the blade. During this period bone grows about and over the blade, and through then holes 220 located in the blade, so as to firmly anchor the blade in place. Subsequently the tissue 301 is reopened.

The post 215 may then be attached to the blade by any convenient means, for example, by cementing them together As an alternative bubbles or score lines may be formed on the walls of the extension 216 of the post or on the interior walls of the cavity 212. Then, when the parts are brought together, a cold weld is formed between the two parts in the manner described with respect to FIGS. 16 and 17.

After the post is installed an artificial tooth 320 or a portion of bridge may be attached to the post. This attachment may be by means of cement, screws or any other convenient fastening means.

With the post shown in FIGS. 20 and 21 it is not necessary to utilize a blade which is wide enough to enclose a threaded neck. Thus it is unnecessary to destroy additional bone to accommodate the typical bolt in the implant blade at the location of the attachment screws. The blade implant thus contains a maximum amount of bone flanking it bucco-lingually. This provides the maximum support against lateral thrusts of the tongue and eccentric movements of the mandible.

An implant such as that shown in FIG. 20 wherein the connection between the blade and the post is by means of a broad, flattened, rectangular neck provides many advantages. Such a connection is far stronger than the narrow screw used in the prior art to connect a post to a widened cylindrical hollow threaded core in the blade. There is also an advantage over the semi-submergible implant wherein a part of the attachment structure sticks out of the gummed tissue during the healing phase. With these designs bacterial invasion can occur and also the structure is clearly weaker in design than the rectangular, long flat neck. This submergible design also allows for total bone regeneration in a totally closed environment. Thus there is better retention of the blade and less opportunity for bacterial infection.

With the design of FIG. 20 the width of the neck along its entire anterior-posterior or mesio-distal length remains the same. Thus there is an equal amount of bone along both the buccal and lingual faces.

After the blade is installed a styrene or Teflon rectangular cap may be located inside the slit 212. This cap prevents bone from growing into the slit during the healing phase. After the blade is firmly anchored in the bone the tissue may be reopened, the plastic cap removed and the permanent post installed. If the posts have minute balls, micro-extensions or sandblasted lines on the extension 216, these can form the basis of a cold weld attachment to the blade. These bubbles or grooves 213 which are located on the extension 216 may have any desired shape. By gentling tapping the extension 216 into slot 212 the bottom surface 219 of the post comes to rest on the top surface 222 of the blade. Thus no neck portion is provided in the overall design which would separate the post from the blade. By eliminating the neck portion the implant structure is made much stronger.

It frequently occurs that the center axis of the densest part of the available bone of a patient is offset from the line along which the natural teeth are positioned. To compensate for this it may be necessary to have the blade and post offset from one another as shown in FIGS. 22A and 22B.

The offset blades are particularly useful when there is a great angulation of the bone morphology. This occurs especially in the maxilla with its tremendous oblique angle off the horizontal plane. For this purpose the taper of the blade is made such that the palatal side of the shoulder is shorter in height than the labial side so that when the post is inserted, the post can be bent so its base is flush with the shoulder. This bend can be an angulation of 15°-30° from the bucco to palatal side. This gives more support to the obliquely angulated post.

If more than one such offset or angulated post is provided on a single blade, only those portions that are at the positions of the vertical slits that support the post need to be angulated.

In FIG. 22A the top surface of the blade 210 and the post 215' are aligned. However, the blade side walls 224, 225 project at an angle to the upper surface.

In the arrangement shown in FIG. 22B the upper surface of the blade is at an angle. Thus, when the bottom of the post part 215" engages the top surface flush, the post 215" is offset at an angle. In order to accomplish this, the left surface 224' is lower than the right surface 225'.

As shown in FIGS. 22A and 22B, the posts are detachable and the slits in which the neck portions of the post are inserted are at different angles. However, this arrangement can also be cast as a single combination of blade and post, but in such circumstances the blade is not submergible.

FIGS. 22A and 22B show cross sections of the offset blades. In front view the blades can have any convenient configuration, e.g., rectangular, triangular, trapezoidal, etc. Also it should be understood that in an arrangement such as shown in FIG. 22B where the top surface of the blade is offset, this offset need be provided only in the area of the blade where the post is connected. Other areas of the top surface of the blade may be horizontal or at some other convenient angle.

FIG. 23 shows a still further embodiment of the present invention. This arrangement provides the benefits of both a blade and screw type dental implant. With this implant a blade body 310 is provided. This blade body has a generally rectangular shape but may be in any other convenient shape. At a position along the upper surface of the blade there is a 360° coronal ring or collar 325. If desired this ring or collar may have internal threads which match the threads of a screw post 330. As shown more clearly in FIG. 25 the coronal ring 325 extends beyond the lateral walls of the blade portion. Below the coronal ring there is a cavity 327 in the blade body which terminates at its lower end in a apical disc or concavity 329.

In utilizing the invention shown in FIGS. 23-25 the blade 310 is inserted in a conventional manner in a groove formed in the patent's bone. The top portion of the groove, however, at the location of the coronal ring 325, may be expanded to accept the ring as shown in FIG. 24 at location 330. Then the blade is located in the groove. Either immediately or at a subsequent time when the blade has become fused with the surrounding bone, a threaded post 315 is inserted through the coronal ring 325 and is threaded downwardly. This post 315 has self-tapping threads which extend outwardly into the bone on either side of the blade, thus making a threaded connection therewith.

Post 315 is sized such that when it is threaded completely into the bone and the blade, the end of the post rests in the apical disc 329 as shown most clearly in FIG. 24. The post may be cemented into the cavity 327 shown in FIG. 23. To aid this, fenestrations can be provided on the top surface or shoulder of the blade adjacent the conical ring 325 to allow better adhesion of the cement.

With the arrangement of FIG. 23 the anchoring effects of a blade and a screw are combined to provide a particularly strong attachment to the bone. The threads within collar 325 are primarily used to guide post 315 into the surrounding bone and toward the apical disc 329. However, these threads are not totally necessary and can be eliminated.

The screw illustrated in FIG. 23 may be 2.5 mm in diameter or larger depending on the bone width to be penetrated. As noted the threads of this screw may contact internal threads in coronal ring 325. Further, threads may be provided along the internal surface of cavity 327 to further guide the screw towards the apical disc 329. The threads along the cavity surface 327 are at the mesial third and distal third of the cavity, so the cavity is mostly open to the adjacent bone along its middle buccal and middle lingual third. This allows the screw implant to self-thread itself through the length of the internally threaded blade on its mesial and distal sides. The buccal and lingual thirds of the screw 315 self-tap within the surrounding bone that flanks it buccally and lingually.

While only a single screw is shown in the blade of FIG. 23, it is within the scope of the invention to provide two or more such threaded post arrangements along a single blade.

As shown in FIGS. 23 and 24 the screw and the blade taper towards the apical disc. However, both the blade and screw may be rectangular in cross section if desired It is possible to make the post portion 335 of screw post 315 separate from the screw portion 333. In such a case, screw part 333 can be inserted into the ring 325 and cavity 327 so that the combination is totally submergible In such a situation a recess 337 (FIG. 24) can be provided in the screw to be utilized in rotating the screw into place. After the blade and screw are firmly in place a plastic cap can be inserted in recess 337 and the tissue can be sutured over the combination. Then new bone is permitted to grow about them. Subsequently this tissue can be opened and the cap removed. The post portion 335 can next be attached to the screw part 333, perhaps by a projection from post 335 that extends into slot 337. This attachment can be by adhesive or by a cold weld joint formed by the crushing of micro-bubbles located on the projection from post 335. Other attachment means may also be used. This attachment can be, for example, by means of screw threads located within slot 337 which are engaged by a threaded shaft at the base of post 335. In an alternative embodiment the upper portion of screw 333 may contain external threads and the posts may be screwed down over these external threads by means of a threaded collar projecting from the base of the post. In such a case it may be necessary to remove the coronal ring by a drill to allow access to the thread of the upper portion of the screw (now shown).

A post 380 may be utilized in place of post 315 in the embodiment of FIG. 23A. Post 380 does not have a threaded section. Instead its lower section 383 is generally a cylinder 382 with projections 384 spaced about its circumference. The lower ends of the projections are provided with knife edges 385.

With post 380 there is no need for threads on the ring 325 or in the cavity 327. When the blade is installed a drill is used to cut away some of the bone on the buccolingual sides of the cavity at a diameter slightly larger than cylinder 383. Then the post 380 is tapped into place. During this procedure the edges 385 cut vertical grooves into the surrounding bone. When in place, the post 380 resists turning because the projections 384 are trapped in the grooves. This allows an artificial tooth structure to be connected to the post by a vertical screw without loosening the implant due to turning force.

In addition to the implant 380 shown in FIG. 23A, other types of non-threaded "tap in" implants, such as Calcitite, IMZ, bullet, etc. may be used with the present invention.

Figure 27:
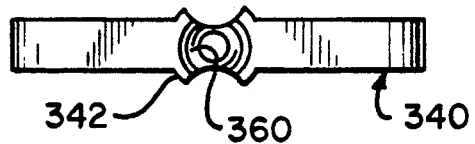
FIG. 27 is a top view of the blade of FIG. 26.

The implant shown in FIGS. 26 and 27 is similar to that shown in FIGS. 23-25. However, in the implant of FIGS. 26-27 the body of the blade 340 has a bulge 342 at the location where the screw 350 engages the threaded cavity 360 in the blade. Portions of the cavity 360 are removed so that the threads of screw 350 extend into the flanking bone and provide a secure anchoring of the blade and screw in the bone in much the same manner as the arrangement shown in FIGS. 23-25. This body bulge gives somewhat more support and guidance to the screw 350 than in the arrangement shown in FIG. 23.

In any of the arrangements shown with detachable posts, the post can be arranged such that it does not rest on the top surface of the blade and there is a small amount of neck available. This may aid in attaching the artificial tooth to the post. However, because of the increased strength of the neck as shown in the arrangements of at least FIGS. 20-27, the allowance for a neck does not significantly weaken the overall implant. However, when the post rests on the upper surface of the shoulder of the blade, there is increased lateral support for the post.

Figure 28:
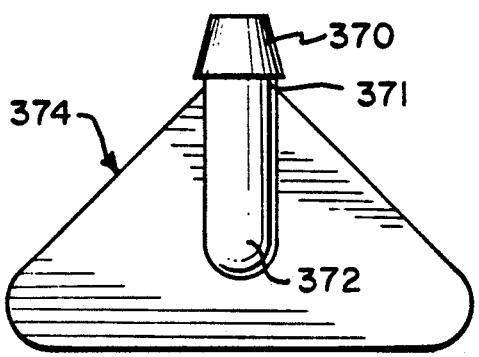
FIG. 28 is a side view of an implant with a body bulge which has a one-piece blade and post.
Figure 29:
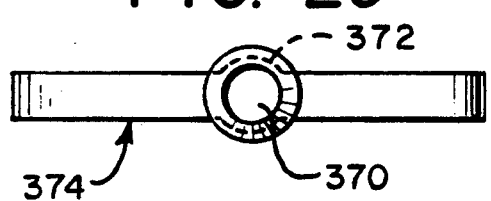
FIG. 29 is a top view of the implant of FIG. 28.

FIGS. 28 and 29 show a one piece semi-submergible implant with a completely rounded or elliptical post 370 which is continuous with a body bulge 372 on the implant body 374. The body bulge acts to give strength to the neck part 371 which supports the post part 370. This one piece design allows for immediate fixation but has an improved neck design. If desired, the post part 370 may be made detachable from the blade. In this case the blade is submergible and may be attached to the blade by matching screw threads on each piece. The bulge provides additional width to the blade near its upper part to support the screw post and the post is made wide and without a neck to give it greater strength.

Figure 30A:
FIG. 30A is a front view of another embodiment of a post for the submergible blade of FIG. 30.
Figure 30:
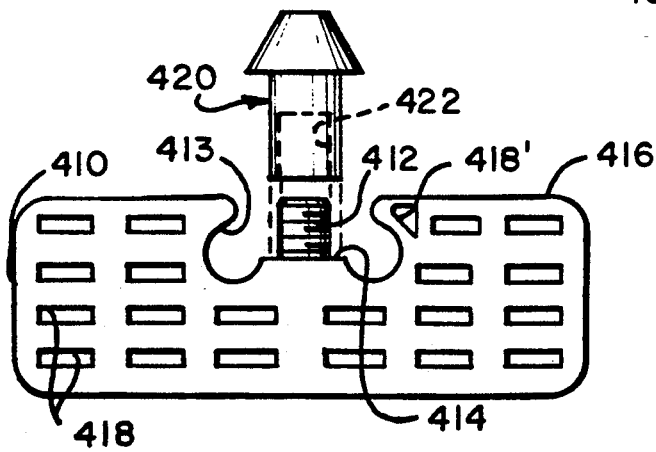
FIG. 30 is a front view of a submergible blade with a recessed threaded connection part.

FIG. 30 is a further example of a submergible blade 410 without a weak neck part on its detachable post 420. The post 420 is connectible to a connection part 412 which is in the form of a projection with a threaded cavity at its end. In cross section the blade 410 may be rectangular, tapered or some other suitable shape.

The projection 412 extends toward the occlusal plane from the bottom surface 414 of a recess 413 in the blade. The end of this projection is at about the level of the upper or superior surface 416 of the blade. As a result, when the blade is buried in the bone, either no part of the projection 412 or very little sticks out of the hole in the bone. This allows the gum tissue to be placed over the protection, even after a plastic cap 430 is secured over the projection.

The plastic cap 430 has a cavity 432 which allows it to seat well down on the projection. The cavity may have threads which match those of projection 412. Thus the cap can be threaded onto the projection. Alternatively, if the cap 430 is flexible, it may not have threads in the cavity and may merely be pushed down over the projection.

When the gum tissue is sutured in place over the blade and cap, they remain in place while new bone grows over the top of the blade, except where the cap is located, and through the parallel rows of vents 418 which extend at least part way through the blade. While not necessary, the vents in FIG. 30 are shown to be of substantially equal size and equally spaced. Other arrangements are also possible, e.g. vents 418' (in dotted line) may be made to conform to the area of the blade near the post.

When healing is complete, bone has grown all around the blade and into the recess 413, except where the cap is located. This bone even covers the undercut region of the recess 413 near the surface 416.

At this point the cap is removed and replaced with the post 420, which post may have a threaded cavity 422 for attachment to projection 412. This post is long enough to stick up out of the gum and provide a mounting surface for an artificial tooth or bridge.

The base surface 414 is very broad and is at least as wide as the blade. Thus it provides a strong support for the post 420. The projection 412 may even be wider than the blade so that the post and projection are very strong and form a bulge in the overall implant at the site of the post.

While only one post 420 and connection part 412 are shown in the embodiment of FIG. 30, it should be understood that two or more may be provided on a single blade. Also the spacing between the projection 412 and the edge of recess 413 may be different distances, but a distance of about 15 mm is preferred. The depth of the recess 413 may also be varied as suitable.

Figure 31:
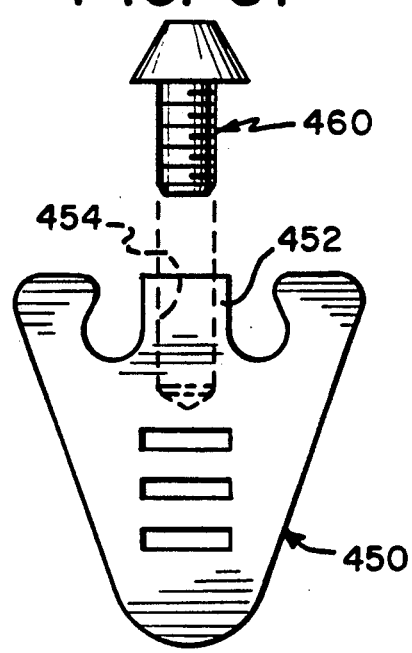
FIG. 31 is an alternative arrangement of the implant of FIG. 30.

A rectangular blade is shown, in FIG. 30. However, this invention may be utilized with blades of various shapes. For example, the blade 450 of FIG. 31 is an inverted triangle.

Figure 31A:
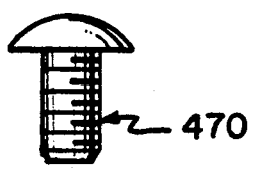
FIG. 31A is a front view of another embodiment of a post for the implant of FIG. 31.

The blade 450 is substantially like the blade 410 in FIG. 30. However, instead of external threads on the connection part 452, it has a projection with an internally threaded cavity 454. A cap 470 (FIG. 31A) with matching external threads and a post 460 with matching external threads are used with blade 450.

What is claimed is:

1. An oral implant for supporting an artificial tooth structure, comprising:
   a generally solid implant portion with a top surface and a bottom, said implant portion having at least one connection part forming a part of the top surface of the implant portion, said connection part does not extend substantially above the top surface of the implant portion, said connection part having longitudinal sides and generally orthogonal ends, the distance between the sides of the connection part being as wide as the lateral dimension of the rest of the implant portion at the top surface, said implant portion being adapted to be fitted in an opening in a bone in the vicinity of the occlusal plane of a patient in such a manner that the connection part is towards a rim of the opening in the bone; and
   at least one post portion having first and second ends, the first end being adapted to receive the artificial tooth structure and the second end being rigid and adapted for a direct connection to the connection part of the implant portion, the second end of said post portion having lateral dimensions such that a part of the second end extends outwardly at least substantially as far as the sides of the connection part, and longitudinal dimensions that extend over the major portion of the distance between the ends of the connection part;
   said implant portion having bucco-lingual side surfaces in the mesio-distal plane connected with the top surface along a connection edge, the connection edge sloping toward the bottom of said implant portion in the direction away from the connection part such that the top surface is substantially below the rim, whereby bone may grow over said implant portion up to the connection part and no narrow neck portion is provided between said post portion and said implant portion.

2. An oral implant according to claim 1, wherein said implant portion has a substantially triangular configuration, the connection part of the implant portion being positioned at the apex of the triangle.

3. An oral implant according to claim 1, wherein said portion defines shoulders at the second end which overlap surfaces of said connection part of the implant portion in the bucco-lingual and mesial-distal directions.

4. An oral implant according to claim 1, wherein said post portion lateral dimensions at the second end that exceed those of the connection part so as to form shoulders that extend beyond the implant portion.

5. An oral implant according to claim 1, wherein the implant portion in the bucco-lingual direction has a wedge-shaped configuration with wide and narrow ends, the side end being connected to the second end of the post portion.

6. An oral implant according to claim 1, wherein said implant portion further comprises bending means to enable the oral implant to be bent in the buccal-lingual direction, said bending means being in the form of at least one recess along the mesio-distal length of the connection part.

7. An oral implant according to claim 1, wherein a median vertical axis of the post portion is at an angle to a median vertical axis of the implant portion in the buccal-lingual plane.

8. An oral implant according to claim 1, wherein the first end of the post portion has receiving means for receiving a fastener means for fastening the artificial tooth structure to the post portion.

9. An oral implant according to claim 8, wherein the receiving means is an opening having an internal thread and adapted to receive a threaded shaft extending from the artificial tooth structure.

10. An oral implant according to claim 9, wherein the receiving means opening has a longitudinal axis generally parallel to the occlusal plane when the implant is installed.

11. An oral implant according to claim 9, wherein the receiving means opening has a longitudinal axis generally perpendicular to the occlusal plane when the implant is installed.

12. An oral implant according to claim 1, wherein there are a plurality of connection parts spaced along the implant portion and a plurality of post portions attached to separate areas of the connection parts.

13. An oral implant according to claim 1, wherein said implant portion and said post portion are made from the same material, and the material is one of the group of titanium, vitalium or surgical stainless steel and covered with hydroxylapatite.

14. An oral implant according to claim 1, wherein said post portion is detachably connected to said implant portion 15. An oral implant according to claim 14, wherein said connection part has a projection and said post portion has a mating cavity, and further including means for fastening the projection in said cavity.

16. An oral implant according to claim 15, wherein the means for fastening is an adhesive.

17. An oral implant according to claim 15, wherein the means for fastening is a fastening rod penetrating said post portion and the projection of said connection part.

18. An oral implant for supporting an artificial tooth structure as in claim 1 wherein the lateral dimension of the connection part is wider than the lateral dimension of the rest of the implant portion.

19. An oral implant according to claim 18 wherein the lateral dimension of the second end of the post portion extends outwardly further than the sides of the connection part.

20. A semi-submergible implant for supporting an artificial tooth structure, comprising:
a generally solid implant portion having a top and bottom, a connection part with lateral and longitudinal dimensions being provided at the top of the implant portion, said implant portion being adapted to be fitted in an opening in the bone in the vicinity of he occlusal plane of a patient in such a manner that said implant portion is submerged below a rim of the opening and at least a portion of the connection part extends outwardly beyond the rim in the direction of the occlusal plane, the extent of the connection part being limited such that when the implant portion is installed in a bone of a patient the connection part may be covered by the patient's gum tissue; and
at least one post portion having first and second ends, said first end being adapted to receive at least a part of the artificial tooth structure and the second end being rigid and adapted for a direct connection to the connection part, the second end of said post portion having a lateral dimension at least as wide as the lateral dimension of the connection part and a longitudinal dimension that extends over the major portion of the longitudinal dimension of the connection part;
said implant portion having bucco-lingual side surfaces in the mesio-distal plane connected with the top, along a connection edge, the connection edge sloping toward the bottom in the direction away from the connection part such that the top of the implant portion is substantially below the rim, whereby bone may grow over said implant portion up to the connection part and no narrowed neck portion is provided between said post portion and said implant portion.

21. A semi-submergible oral implant according to claim 20, wherein said post portion has a fastening member extending outwardly from the second end and said connection part has a opening for receiving of said fastening member.

22. A semi-submergible oral implant according to claim 21, wherein the fastening member and the opening in the connection part have threads for mutual engagement.

23. A submergible oral implant for supporting an artificial tooth structure, comprising:
an implant portion having a top and bottom, and being adapted to be fitted in an opening in the bone of a patient in the vicinity of the occlusal plane such that it is submerged below the rim of the opening, said implant portion having an upper surface at the top which is directed toward the occlusal plane when the implant portion is installed in the opening, the upper surface having at least one groove therein which extends in the mesial-distal direction and penetrates the implant portion a substantial distance towards the bottom of the opening,
at least one post portion having a first end for receiving at least part of an artificial tooth structure and a second end from which a projecting part extends, said post portion between the first and second ends having substantially the same longitudinal dimension as the projecting part, the projecting part being adapted to fit within the groove, the longitudinal mesial-distal dimension of the projecting part and the groove being significantly greater than their lateral dimension, said post portion extending significantly above the patient's bone and gum tissue when installed on said implant portion;

said implant portion having bucco-lingual side surfaces in the mesio-distal plane connected with the upper surface along a connection edge, the connection edge sloping toward the bottom of said implant portion in the direction away from the connection part such that the upper surface is substantially below the rim, whereby bone may grow over said implant portion up to said post portion and no narrow neck portion is provided between said post portion and said implant portion.

24. An oral implant according to claim 23 wherein the lateral dimension of the second end is at least substantially as great as the lateral dimension of the upper surface of said implant portion, the projecting part and the groove being dimensioned such that the second end may rest on the upper surface when the projecting part is fully inserted into the groove.

25. An oral implant according to claim 24, wherein the groove and the projection part are tapered to be wider in the direction of the upper surface.

26. An oral implant according to claim 24, wherein a median axis of the implant portion is at an angle to a median axis of the post portion.

27. An oral implant according to claim 26, wherein the upper surface is generally parallel to the occlusal plane.

28. An oral implant according to claim 26, wherein the upper surface is at an angle to the occlusal plane.

29. A submergible oral implant for supporting an artificial tooth structure, comprising:

an implant portion adapted to be fitted in an opening in the bone of a patient in the vicinity of the occlusal plane such that it is submerged below the rim of the opening, said implant portion having an upper surface directed toward the occlusal plane when the implant portion is installed in the opening, said implant portion having a cut out extending from side to side and from the upper surface a significant way toward the opposite surface of the implant portion; and a post having a first end for supporting an artificial tooth structure and a second end, a shaft extending from said second end, said shaft having a diameter larger than the lateral dimension of the implant portion, said shaft being adapted to be inserted into the cut out and threaded into engagement with the bone flanking the cut out so that said second end of said post is in contact with said upper surface of the implant portion, said implant portion and cut out having a size sufficient to guide the shaft into the bone during engagement.

30. A submergible implant according to claim 29, wherein the lateral dimensions of said post are at least substantially as great as the lateral dimensions of the implant portion at the upper surface.

31. A submergible implant according to claim 29, wherein the shaft is threaded, and the cut out is provided with threads that mate with the threads of the shaft.

32. A submergible implant according to claim 29, further including a coronal ring at the upper surface where the cut out is located in order to receive and guide the shaft.

33. A submergible implant according to claim 32, wherein the shaft is threaded, and the coronal ring has threads that mate with the threads of the post shaft.

34. A submergible implant according to claim 32, wherein the base of the cut out has an apical disc to receive the end of the shaft and to guide it in place.

35. A submergible implant according to claim 29, wherein the shaft is threaded, the cut out is provided with threads, and further including an apical disc at the base of the cut out and a threaded coronal ring at the location along the upper surface where the cut out ends, the threads of the cut put and the coronal ring mating with the threads of the shaft.

36. A submergible implant according to claim 29, wherein the post is detachable from the shaft and further including means for fastening the shaft to the post 37. A submergible implant according to claim 36, wherein the lateral dimensions of said post are at least as great as the lateral dimensions of the upper surface of the implant portion.

38. A submergible implant according to claim 29, wherein the implant portion has a lateral bulge at the location of the cut out.

39. A submergible oral implant for supporting an artificial tooth structure, comprising:

an implant portion adapted to be fitted in an opening in the bone of a patient in the vicinity of the occlusal plane such that it is submerged below the rim of the opening, said implant portion having an upper surface directed toward the occlusal plane when the implant portion is installed in the opening and a bottom at the opposite surface, said implant portion having a recess extending from side to side and from the upper surface a significant way toward the bottom of said implant portion;

said implant portion including a connection part in the form of a projection from a base surface of the recess, the projection extending only to the vicinity of the upper surface of said implant portion; and a post separate from said implant portion and having a shaft extending from one end, the shaft being connectable to the connection part projection;

the implant portion having bucco-lingual side surfaces in the mesio-distal plane connected with the upper surface, the side surfaces at their connection to the upper surface sloping toward the bottom of said implant in the direction away from the connection part such that the upper surface is substantially below the rim, whereby bone may grow over said implant portion up to the connection part and no narrow neck portion is provided between the connection part and said implant portion.

40. A submergible implant according to claim 39 wherein the shaft of the post has external threads and the connection part projection has a cavity with mating internal threads such that said post may be connected to said connection part via the mating threads.

41. A submergible implant according to claim 39 wherein the shaft of the post has a cavity with internal threads and the connection part projection has external mating threads such that said post may be connected to said connection part via the mating threads.

42. An oral implant for supporting an artificial tooth structure, comprising:

an implant portion adapted to be fitted in an opening in the bone of a patient in the vicinity of the occlusal plane, said implant portion having a bulge in its bucco-lingual side surfaces and an upper surface directed toward the occlusal plane when the implant portion is installed in the opening, the upper surface of the bulge being substantially no higher than that of the adjacent areas of the implant portion; and a post in contact with and extending from the upper surface of the implant portion at the location of the bulge, the lateral dimensions of said post adjacent the upper surface of the implant portion being at least substantially as great as the lateral dimension of the upper surface of the bulge; the bucco-lingual side surfaces being connected with the upper surface, the side surfaces at their connection to the upper surface sloping toward the bottom of said implant in the direction away from the bulge such that the upper surface is substantially below the rim, whereby bone may grow over the implant portion up to said post and no narrow neck portion is provided between said post and said implant portion.

43. An oral implant according to claim 42 wherein the post is detachable from the implant portion.

* * * * *